(12) United States Patent
Gandhi et al.

(10) Patent No.: US 8,911,787 B2
(45) Date of Patent: Dec. 16, 2014

(54) STABLE ORAL BENZIMIDAZOLE COMPOSITIONS AND PROCESS OF PREPARATION THEREOF

(71) Applicant: Ranbaxy Laboratories Limited, Delhi (IN)

(72) Inventors: Rajesh Gandhi, Gurgaon (IN); Chayapathy Issa, Chittoor (IN); Vishnubhotla Nagaprasad, Hyderabad (IN)

(73) Assignee: Ranbaxy Laboratories Limited, New Delhi (IN)

( * ) Notice: Subject to any disclaimer, the term of this patent is extended or adjusted under 35 U.S.C. 154(b) by 0 days.

(21) Appl. No.: 14/150,058

(22) Filed: Jan. 8, 2014

(65) Prior Publication Data

US 2014/0134259 A1    May 15, 2014

Related U.S. Application Data

(62) Division of application No. 11/722,731, filed on Feb. 26, 2008, now Pat. No. 8,658,216.

(51) Int. Cl.
*A61K 31/4439* (2006.01)
*A61K 9/50* (2006.01)

(52) U.S. Cl.
CPC ........... *A61K 31/4439* (2013.01); *A61K 9/5078* (2013.01)
USPC ........................................................ 424/494

(58) Field of Classification Search
None
See application file for complete search history.

(56) References Cited

U.S. PATENT DOCUMENTS

| | | | |
|---|---|---|---|
| 4,255,431 A | 3/1981 | Junggren et al. | 424/263 |
| 4,738,974 A | 4/1988 | Brandstrom | 514/338 |
| 4,786,505 A | 11/1988 | Lovgren et al. | 424/468 |
| 4,853,230 A | 8/1989 | Lovgren et al. | 424/466 |
| 5,385,739 A | 1/1995 | Debregeas et al. | 424/494 |
| 5,626,875 A | 5/1997 | Ballester Rodes et al. | 424/464 |
| 5,690,960 A | 11/1997 | Bengtsson et al. | 424/480 |
| 5,877,192 A | 3/1999 | Lindberg et al. | 514/338 |
| 5,900,424 A | 5/1999 | Kallstrom et al. | 514/338 |
| 6,159,499 A | 12/2000 | Seth | 424/451 |
| 6,207,198 B1 | 3/2001 | Seth | 424/494 |
| 6,274,173 B1 | 8/2001 | Sachs et al. | 424/480 |
| 6,564,113 B1 | 5/2003 | Barto et al. | 700/99 |
| 6,602,522 B1 | 8/2003 | Chen et al. | 424/480 |
| 6,713,495 B1 | 3/2004 | Sherman | 514/338 |
| 2002/0128293 A1 | 9/2002 | Rampal et al. | 514/338 |
| 2003/0232861 A1 | 12/2003 | Sherman | 514/338 |
| 2005/0129760 A1* | 6/2005 | Muskulus et al. | 424/470 |

FOREIGN PATENT DOCUMENTS

| | | | | |
|---|---|---|---|---|
| CA | 2502219 | 4/2004 | ......... | A61K 31/4439 |
| IN | 1494/DEL/2003 | * 11/2003 | | |
| WO | WO 2004/002982 | 1/2004 | ......... | C07D 401/12 |
| WO | WO 2004/037253 | 5/2004 | ......... | A61K 31/4439 |
| WO | WO 2004/066982 | 8/2004 | ............... | A61K 9/30 |
| WO | WO 2006/002077 | 1/2006 | ............... | A61K 9/50 |

OTHER PUBLICATIONS

Sorasuchart (Drug Release from Spray Layered and Coated Drug-Containing Beads: Effects of pH and Comparison of Different Dissolution Methods, Drug Development and Industrial Pharmacy, vol. 25, No. 10, pp. 1093-1098, 1999).*

Sorasuchart et al, "Drug Release from Spray Layered and Coated Drug-Containing Beads: Effects of pH and Comparison of Different Dissolution Methods", *Drug Development and Industrial Pharmacy*, 25(10):1093-1098 (1999).

* cited by examiner

*Primary Examiner* — Adam C Milligan

(57) ABSTRACT

The present invention relates to stable oral compositions of one or more benzimidazole compounds and processes for their preparation. Also provided are methods for treating various gastrointestinal disorders.

16 Claims, 2 Drawing Sheets

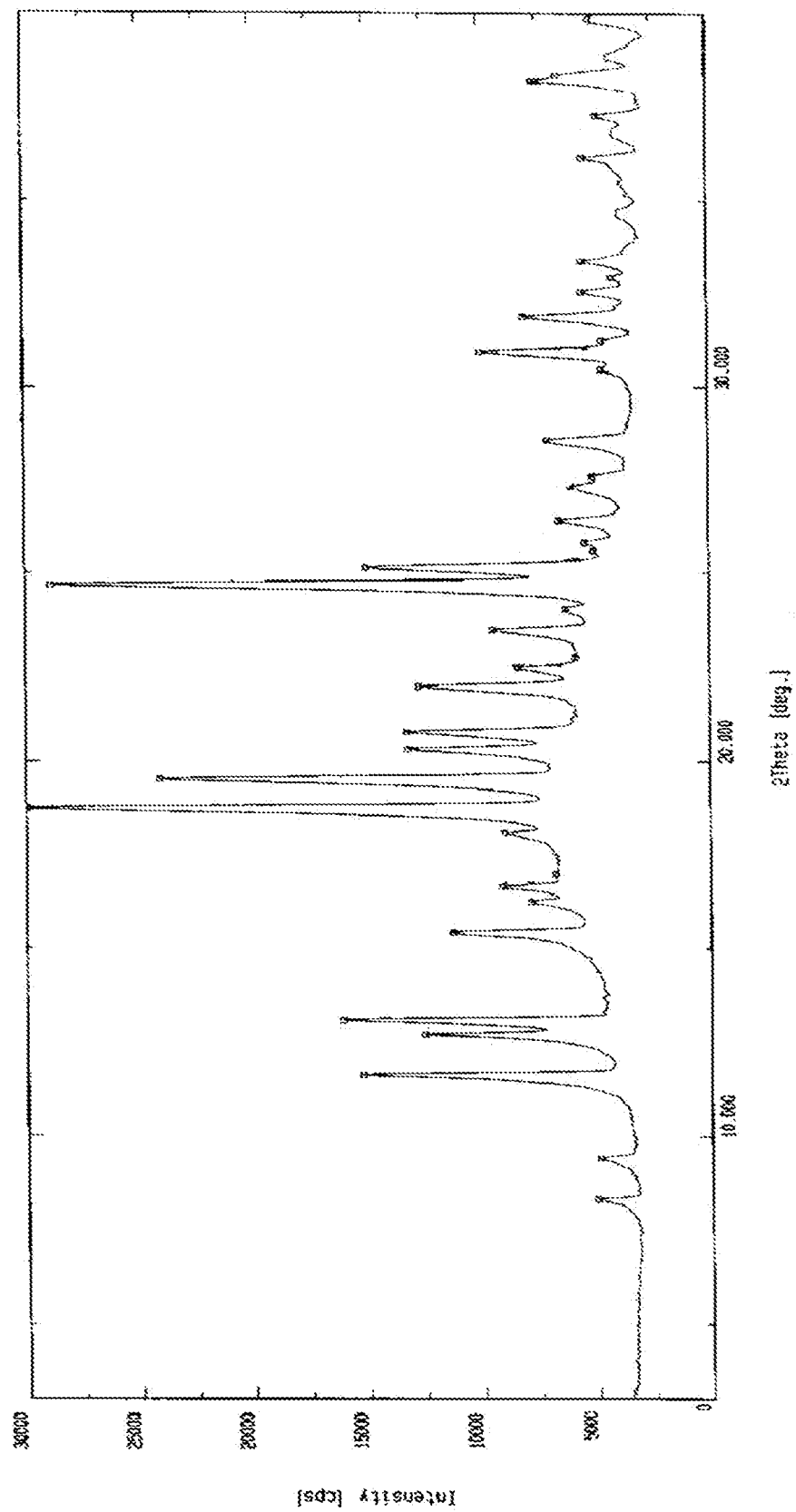

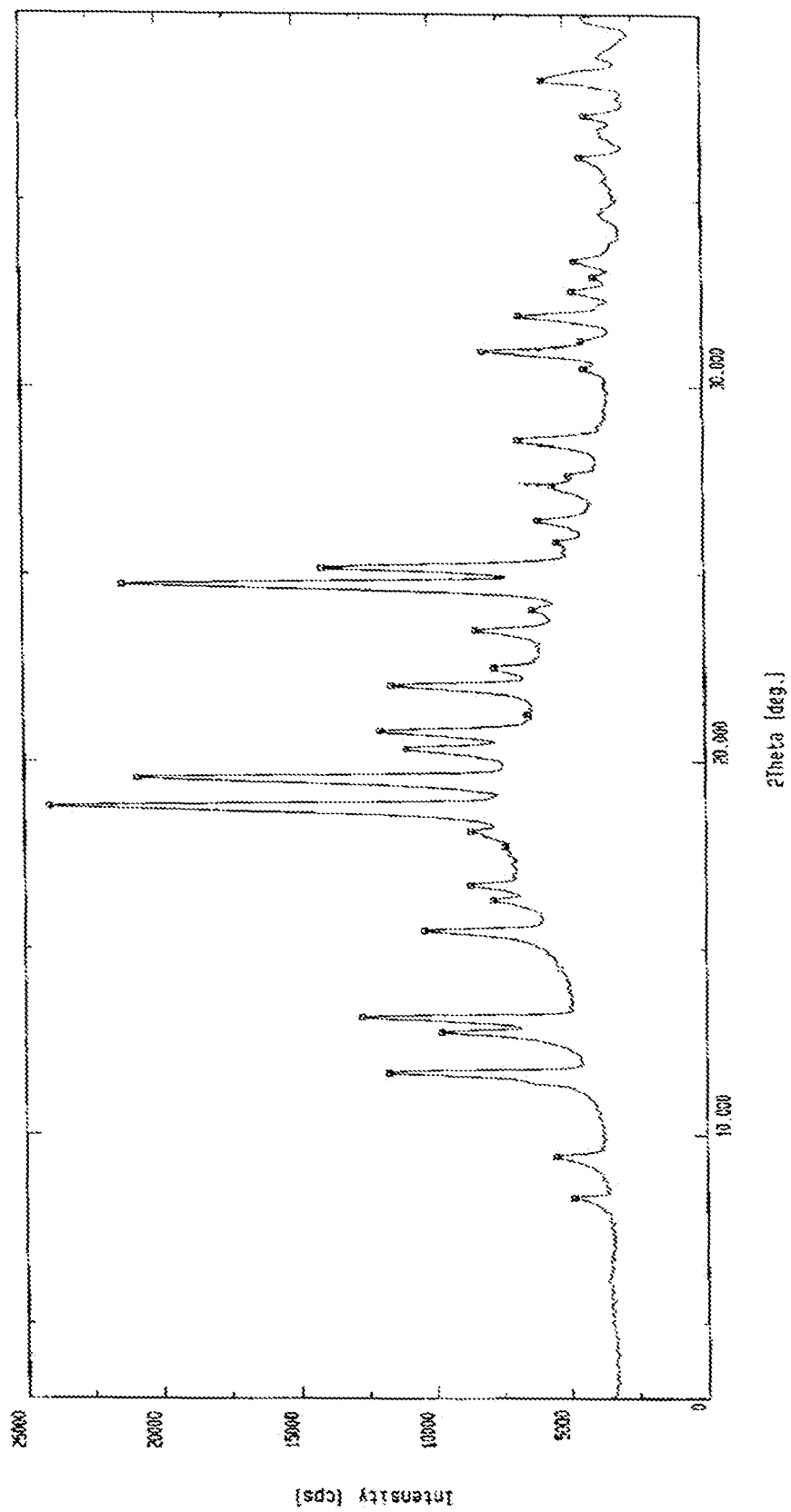

STABLE ORAL BENZIMIDAZOLE COMPOSITIONS AND PROCESS OF PREPARATION THEREOF

TECHNICAL FIELD OF THE INVENTION

The present invention relates to stable oral compositions of one or more benzimidazole compounds and processes for the preparation thereof. Also provided are methods for treating various gastrointestinal disorders.

BACKGROUND OF THE INVENTION

Benzimidazole compounds, such as omeprazole, lansoprazole, pantoprazole, rabeprazole or single enantiomers thereof are strong inhibitors of proton pump and are widely used as therapeutic agents for stomach ulcer, duodenal ulcer, and gastro esophageal reflux disorders. Benzimidazole compounds effectively inhibit gastric acid secretion.

U.S. Pat. No. 4,255,431 discloses omeprazole and therapeutically acceptable salts thereof. The advantages of providing the salts of omeprazole and particularly the magnesium salt are disclosed in U.S. Pat. No. 4,738,974.

The single isomers of omeprazole are reported to be more useful in therapy when compared to the racemic omeprazole. U.S. Pat. No. 5,877,192 discloses the use of the (−)-enantiomer of omeprazole (esomeprazole), or a pharmaceutically acceptable salt thereof, in the treatment of gastric acid related diseases as a means to decrease inter-individual variation in plasma levels compared to omeprazole. The use of the (−)-enantiomer of omeprazole to receive increased average plasma levels (AUC) of the substance compared to those of racemic omeprazole and thereby a higher dose efficiency is also disclosed in the patent.

U.S. Pat. No. 5,900,424 discloses omeprazole magnesium salt as having a degree of crystallinity that is higher than 70% as determined by x-ray powder diffraction. The patent teaches that the isolation and purification in full manufacturing scale of the magnesium omeprazole salt as per U.S. Pat. No. 4,738,974 presents a major problem. The magnesium omeprazole salt crystals so obtained by this method are very fragile. The patent further teaches that in order to use the magnesium salt of omeprazole in full manufacturing scale in preparing pharmaceutical formulations primarily for oral administration, such as tablets, it is necessary that the magnesium omeprazole possess a combination of properties. This makes such full scale manufacturing feasible. These physical properties include degree of crystallinity, particle diameter, density, hygroscopicity, water content and content of other solvents. U.S. Pat. No. 5,690,960 teaches stable oral formulation comprising a core containing a magnesium salt of omeprazole wherein the salt has more than 70% crystallinity as determined by x-ray powder diffraction; a subcoating layer; and an enteric coating layer.

The efforts to stabilize benzimidazole compositions using amorphous form of benzimidazole compounds are reported in prior art. WO 2004/037253, assigned to Ranbaxy Laboratories and WO 2004/002982, assigned to Dr. Reddy's Laboratories teach processes of preparing amorphous forms of a salt of esomeprazole.

U.S. Pat. No. 6,713,495 discloses magnesium omeprazole having a degree of crystallinity of less than 67% by weight and having a residual organic solvent content of less than 7% by weight. U.S. Patent Application No. 2003/0232861 discloses magnesium s-omeprazole having a degree of crystallinity of less than 67%. Example 3 of U.S. Pat. No. 6,713,495 and U.S. Patent Application No. 2003/0232861 disclose magnesium omeprazole and magnesium esomeprazole respectively, having a degree of crystallinity less than 25%.

Indian Application No. 1494/DEL/2003, assigned to Ranbaxy Laboratories, discloses stable oral benzimidazole compositions. The compositions include a core comprising amorphous or crystalline benzimidazole compound, a substantially water-insoluble and substantially non-disintegrating separating layer and an enteric coating.

U.S. Patent Application No. 2002/0128293 teaches stable oral pharmaceutical compositions that include omeprazole and a stabilizing excipient, wherein the composition is free of alkaline compounds. Example 7 of the patent application discloses a process of wet drug layering of an inert carrier using a Wurster fluid bed apparatus.

Because of the strong tendency of benzimidazole compounds to decompose in a neutral and in particular, an acidic environment, numerous approaches have been tried to form a stable pharmaceutical formulation comprising such compounds. The acid labile benzimidazole compounds react with both the gastric acid in the stomach and the enteric coatings used for preventing the benzimidazole compound from coming into contact with the gastric acid.

The prior art teaches various approaches to prepare the stable formulations containing benzimidazole compounds. Amongst the most common approaches to stabilize benzimidazole is the use of an alkaline core, separating layer and enteric coating. It is a well-recognized fact that using an alkaline medium in the core stabilizes benzimidazole from acid degradation. Prior art efforts to stabilize a benzimidazole with an alkaline core without a separating layer between the core and the enteric coating was not effective. Thus the recognition of using a layer to separate the alkaline core from the acidic enteric coating was the subject matter of U.S. Pat. No. 4,786,505 and U.S. Pat. No. 4,853,230. The separating coating disclosed in these patents was essentially made up of water-soluble polymeric substances.

U.S. Pat. Nos. 6,274,173; 6,602,522; 5,385,739; 5,626,875; 6,159,499 and 6,207,198 disclose various other formulation approaches to stabilize benzimidazole compositions.

However, there is still a need for the development of new pharmaceutical compositions of benzimidazole compounds with enhanced stability. It was surprisingly observed that careful control of some of the processing parameters is critical to prevent the conversion of the amorphous form of benzimidazole compound to the crystalline form.

The present invention thus relates to the stable oral amorphous benzimidazole compositions and process for preparing the same as herein below described and exemplified.

SUMMARY OF THE INVENTION

In one general aspect there is provided a stable oral benzimidazole composition comprising a benzimidazole core in the form of bead, the core comprising a pharmaceutically acceptable inert carrier coated with one or more amorphous benzimidazole compounds and one or more pharmaceutically acceptable additives; a separating layer surrounding the core; and an enteric coating surrounding the separating layer, wherein the composition contains less than about 30% by weight of crystalline benzimidazole.

Embodiments of the present invention may include one or more of the following features. For example, the benzimidazole compound may be one or more of omeprazole, lansoprazole, rabeprazole, pantoprazole, leminoprazole, pariprazole, single enantiomers, pharmaceutically accepted salts, solvates or mixtures thereof.

The pharmaceutically acceptable additive may include one or more of binders, diluents, disintegrants, lubricants and wetting agents. The binder may be one or more of cellulose derivatives, gums, water-soluble vinylpyrrolidone polymers, and sugars. The diluent may be one or more of sugars, sugar alcohols, cellulose derivatives, and starches. The disintegrant may be one or more of sodium starch glycolate, croscarmellose sodium, crospovidone, corn starch and mixtures thereof. The lubricant may be one or more of magnesium stearate, talc, sodium stearyl fumarate, colloidal silicon dioxide and mixtures thereof. The wetting agent may be one or more of sodium lauryl sulphate, polysorbate 80 and mixtures thereof.

The separating layer may include a substantially water-soluble material. The substantially water-soluble material may be one or more of a substantially water-soluble polymer and a substantially water-soluble excipient. The water-soluble polymer may be one or more of hydroxypropyl methylcellulose, hydroxypropyl cellulose, polyvinylpyrrolidone, sodium alginate, sodium carboxymethyl cellulose, copolymer of vinylpyrrolidone and vinyl acetate. The water-soluble excipient may be one or more of lactose, mannitol, sorbitol, sucrose and glucose.

In another general aspect there is provided a process for the preparation of a stable oral benzimidazole composition. The process includes the steps of:
a) preparing a benzimidazole core formed by dispersing one or more amorphous benzimidazole compounds and one or more pharmaceutically acceptable additives in an aqueous or hydroalcoholic medium to obtain a dispersion;
b) spraying the dispersion onto a pharmaceutically acceptable inert carrier;
c) coating the core with a separating layer; and
d) coating the product of step (b) with an enteric coating, wherein the process of preparation of the benzimidazole core substantially prevents the conversion of benzimidazole compound to its crystalline form.

Embodiments of the process may include one or more of the following features. For example, step (a) may include spraying the dispersion on the pharmaceutically acceptable inert carrier at a bed temperature of less than about 50° C. Step (a) may include spraying the dispersion on the pharmaceutically acceptable inert carrier, such that the total spraying time is less than about 24 hrs. The dispersion of step (a) may be prepared in more than one lot.

The one or more benzimidazole compounds may include one or more of omeprazole, lansoprazole, rabeprazole, pantoprazole, leminoprazole, pariprazole, single enantiomers, pharmaceutically accepted salts, solvates or mixtures thereof. The pharmaceutically acceptable additive may include one or more of binders, diluents, disintegrants, lubricants and wetting agents. The separating layer may include a substantially water-soluble material.

In another general aspect there is provided a method of inhibiting gastric acid secretion in a patent in need thereof. The method includes administering to a patient in need thereof a stable oral benzimidazole composition comprising:
a) a benzimidazole core in the form of bead, the core comprising an pharmaceutically acceptable inert carrier coated with one or more amorphous benzimidazole compound and one or more pharmaceutically acceptable additives;
b) a separating layer surrounding the core; and
c) an enteric coating surrounding the separating layer, wherein the composition contains less than about 30% by weight of crystalline benzimidazole.

BRIEF DESCRIPTION OF THE DRAWINGS

FIG. 1 shows the X-ray diffraction pattern of the composition prepared according to Example 5.

FIG. 2 shows the X-ray diffraction pattern of the composition prepared according to Example 5 after storage at 40° C. and 75% RH for 3 months.

DETAILED DESCRIPTION OF THE INVENTION

The term 'benzimidazole compound' as used herein refers to any of the compounds belonging to the category of benzimidazole used for gastrointestinal disorders and may include one or more of omeprazole, lansoprazole, rabeprazole, pantoprazole, leminoprazole, pariprazole, single enantiomers, pharmaceutically accepted salts, solvates or mixtures thereof. Preferably, the benzimidazole compound may be omeprazole in the form of a pharmaceutically acceptable alkaline salt. More preferably, omeprazole may be in the form of omeprazole magnesium or esomeprazole magnesium. Preferably, the benzimidazole compound is in substantially amorphous form.

The term 'substantially amorphous' refers to having less than 30% crystalline compound by weight. Amorphous esomeprazole magnesium may be prepared according to PCT Application Nos. WO 2004/037253 and WO 2004/002982, both of which are herein incorporated by reference. However any other suitable method can be used to prepare amorphous esomeprazole magnesium used in the present invention.

The term 'stable oral composition' as used herein refers to the oral compositions of amorphous benzimidazole compounds, which are substantially free from crystalline benzimidazole. Preferably, the stable oral composition contains NMT 30% by weight of crystalline benzimidazole. The suitable method of determining the conversion of the amorphous form to the crystalline form is any method with substantial precision, e.g., X-ray diffraction spectroscopy.

The term 'benzimidazole core' as used herein includes one or more benzimidazole compounds and one or more pharmaceutically acceptable additives which are substantially free from crystalline benzimidazole. Preferably, the benzimidazole core contains NMT 30% by weight of crystalline benzimidazole. The benzimidazole core is prepared under optimized processing conditions in order to prevent the conversion of amorphous benzimidazole to crystalline benzimidazole. Preferably, the conversion to crystalline benzimidazole is less than about 30% by weight. The benzimidazole core may be obtained in the form of granules, pellets, beads or minitablets, which may be further processed to obtain benzimidazole compositions in suitable dosage form. For example, the benzimidazole core may be coated with a separating layer and an enteric coating to obtain a coated core. The coated core may be filled into capsules or compressed into tablets.

The term 'composition' refers to any oral dosage form such as tablet or capsule, comprising the benzimidazole core.

The 'pharmaceutically acceptable additives' may include one or more of binders, diluents, disintegrants, lubricants/glidants and solubilizers/wetting agents.

Suitable diluents may include one or more sugars, such as dextrose, glucose, lactose; sugar alcohols, such as sorbitol, xylitol, mannitol; cellulose derivatives, such as powdered cellulose, microcrystalline cellulose; starches, such as corn starch, pregelatinized starch, or maize starch. The preferred range of diluents depends on the type of composition to be prepared. Some preferred ranges are disclosed in the corresponding examples.

Suitable binders include one or more of cellulose derivatives, such as hydroxypropylmethyl cellulose, hydroxypropyl cellulose, methylcellulose; gums, such as xanthan gum, gum acacia, tragacanth; water-soluble vinylpyrrolidone polymers, such as polyvinylpyrrolidone, copolymer of vinylpyrrolidone and vinyl acetate; sugars, such as sorbitol, mannitol and mixtures thereof. The preferred range of binders depends on the type of composition to be prepared. Some preferred ranges are disclosed in the corresponding examples.

Generally the disintegrants are selected from sodium starch glycolate, croscarmellose sodium, crospovidone, cornstarch or mixtures thereof. The preferred range of disintegrants depends on the type of composition to be prepared. The preferred range is disclosed in the corresponding examples.

Suitable solubilizers/wetting agents may include one or more of sodium lauryl sulphate, polysorbate 80 or mixtures thereof. The lubricant/glidants may include one or more of magnesium stearate, talc, sodium stearyl fumarate, colloidal silicon dioxide and mixtures thereof.

The benzimidazole core is prepared using an optimized process in order to prevent the conversion to crystalline benzimidazole. The one or more amorphous benzimidazole compounds and one or more pharmaceutically acceptable additives may be dispersed in an aqueous or hydroalcoholic medium to obtain a dispersion. The resulting dispersion may be sprayed on a pharmaceutically acceptable inert carrier in a fluidized bed apparatus, e.g., Wurster coater. The process parameters during the drug loading process should be maintained to prevent the conversion to crystalline benzimidazole compound. The important process parameters include the benzimidazole dispersion media, the total solid content in the dispersion, the total spraying time for the preparation of the benzimidazole core, the number of prepared lots of the dispersion, the inlet temperature and the bed temperature during the preparation of the benzimidazole core, the drying temperature, the ratio of omeprazole to the additive in dispersion and such like. It has been observed that a change in any of these process parameters resulted in the conversion of amorphous benzimidazole compound into crystalline benzimidazole. Particularly, the inlet temperature and the resulting bed temperature maintained during the preparation of the benzimidazole core are found to be important. The following conditions, maintained during the preparation of the core, were found to prevent the conversion of amorphous benzimidazole compound to its crystalline form.

Dispersion media—Aqueous or hydroalcohlic
Total solid content in dispersion—5-20% w/w
Total spraying time for the preparation of benzimidazole core—NMT 24 hrs.
Number of prepared lots of dispersion—more than 1
Bed Temperature during preparation of benzimidazole core—NMT 50° C.
Drying Temperature—NMT 50° C.
Benzimidazole to binder ratio in dispersion—from about 10:1 to about 1:5
Benzimidazole to disintegrant ratio in dispersion—from about 10:1 to about 1:10

The benzimidazole core may also be prepared using a rotor granulator, wherein a mixture comprising amorphous benzimidazole compound and one or more pharmaceutically acceptable additives together with a binder dispersion is sprayed on to a pharmaceutically acceptable inert carrier in a rotor granulator under optimized processing conditions. Alternatively, the amorphous benzimidazole compound may be mixed with pharmaceutically acceptable additive and processed using wet granulation/dry granulation.

The 'pharmaceutically acceptable inert carrier' may include a starch, microcrystalline cellulose or sugar sphere, such as nonpareil sugar seeds.

The separating layer as used herein refers to the layer that separates the core from the enteric coating. The separating layer is made up of substantially water soluble material which is capable of dissolving or forming a gel in contact with water. Such material may include substantially water-soluble polymer and/or substantially water-soluble excipients. In the case when the capsule shell acts as a separating layer, additional application of separating layer would be optional. The enteric coating can directly be layered on the capsule shell in such case.

The substantially water-soluble excipients may include one or more of glucose, lactose, mannitol, sorbitol, sucrose, dextrose and mixtures thereof. The substantially water-soluble polymers may include hydroxypropyl methylcellulose, hydroxypropyl cellulose, polyvinylpyrrolidone, sodium alginate, sodium carboxymethyl cellulose, copolymer of vinylpyrrolidone and vinyl acetate. Preferably, the polymers may be hydroxypropyl methylcellulose, hydroxypropyl cellulose or polyvinylpyrrolidone. The range of such substantially water-soluble polymers depends on the type of compositions to be prepared.

The enteric coating may include polymers, such as cellulose acetate phthalate, hydroxypropyl methylcellulose phthalate, polyvinyl acetate phthalate, carboxymethylethylcellulose, methacrylic acid copolymers, such as, compounds known under the trademarks of Eudragit NE30D, Eudragit L, Eudragit S, Eudragit L 100 55 or mixtures thereof. The enteric coating may also include plasticizers, such as triacetin, triethyl citrate, tributyl sebecate, diethyl phthalate, polyethylene glycol and inert excipients such as talc, titanium dioxide, colloidal silicon dioxide, hydroxypropyl methylcellulose, crospovidone and mixtures thereof.

The compositions of the present invention show substantial absence of crystalline benzimidazole under storage at 40° C. and 75% humidity conditions for a period of at least 1 month, preferably 3 months, more preferably 6 months as determined by X ray diffraction method.

The following non-limiting examples describe the various embodiments of the specification.

EXAMPLE 1

| | | Quantity (mg/capsule) | | |
|---|---|---|---|---|
| S. No | Ingredients | 1A | 1B | 1C |
| A) | Benzimidazole core | | | |
| 1 | Non-pareil seeds (20-25) | 100.0 | 100.0 | 60.0 |
| 2 | Amorphous esomeprazole magnesium | 44.5 | 44.5 | — |
| 3 | Amorphous omeprazole magnesium | — | — | 20.6 |
| 4 | Hydroxypropyl methylcellulose | — | 20.0 | 5.0 |
| 5 | Hydroxypropyl cellulose (HPC-L) | 20.0 | — | 5.0 |
| 6 | Crospovidone (Kollidon CLM) | 30.0 | 30.0 | — |
| 7 | Purified water | qs | qs | qs |
| B) | Separating layer | | | |
| 1 | Hydroxypropyl methylcellulose (HPMC) 5 cps | 14.98 | — | 6.97 |
| 2 | Hydroxypropyl cellulose | — | 14.98 | — |
| 3 | Polyethylene glycol 400 | 1.49 | 1.49 | 0.69 |
| 4 | Talc | 2.98 | 2.98 | 1.4 |
| 5 | Purified water | qs | qs | qs |
| C) | Enteric coat | | | |
| 1 | Methacrylic Acid Copolymer Type C | 39.76 | 39.76 | 18.7 |
| 2 | Polyethylene glycol 400 | 3.98 | — | 1.87 |
| 3 | Triethyl citrate | — | 3.98 | — |

-continued

| S. No | Ingredients | Quantity (mg/capsule) | | |
|---|---|---|---|---|
| | | 1A | 1B | 1C |
| 4 | Talc | 15.11 | 15.11 | 7.1 |
| 5 | Titanium dioxide | 4.7 | 2.7 | 2.22 |
| 6 | Purified water | qs | qs | qs |
| D) | Lubrication | | | |
| 1 | Talc | 0.50 | 0.50 | 0.45 |
| | Total | 278.0 | 276.0 | 130.0 |

Process

A. Preparation of Benzimidazole Core

1. Hydroxypropyl cellulose/hydroxypropyl methylcellulose was dissolved in purified water under mechanical stirring followed by addition of crospovidone and amorphous esomeprazole magnesium/amorphous omeprazole magnesium to obtain a dispersion.

2. The dispersion (prepared in four lots) was sprayed on non-pareil seeds in a Wurster coater for 12-24 hours using the following parameters, while continuing the slow stirring of the dispersion:

Inlet air temperature: 45-60° C.
Bed temperature: 35-40° C.
Pump rpm: 15-25
Atomisation air pressure: 2.0-5.0 kg/cm$^2$ 3. The material of step 2 above was dried at 35-40° C. till the loss on drying is less than 1.5% w/w to obtain the benzimidazole core.

B. Separating Layer

1. Hydroxypropyl methylcellulose/hydroxypropylcellulose were dissolved in purified water under mechanical stirring followed by addition of polyethylene glycol and talc to obtain a coating dispersion.

2. The coating dispersion was sprayed on the benzimidazole core in a Wurster coater using the following parameters, while continuing the slow stirring of the dispersion:

Inlet air temperature: 45-60° C.
Bed temperature: 35-40° C.
Pump rpm: 10-20 [0061]Atomisation air pressure: 2.0-5.0 kg/cm$^2$ 3. The coated core of step 2 above was dried at 35-40° C. for 15 minutes to obtain the coated benzimidazole core.

C. Enteric Coating

1. Polyethylene glycol/triethyl citrate were dissolved in purified water under mechanical stirring followed by addition of titanium dioxide and talc to obtain a dispersion.

2. Methacrylic acid copolymer type C was added to the dispersion of step 1 under mechanical stirring to obtain a coating dispersion.

3. The coating dispersion of step 2 was sprayed on the coated benzimidazole core in Wurster coater using the following parameters, while continuing the slow stirring of the dispersion:

Inlet air temperature: 40-50° C.
Bed temperature: 30-35° C.
Pump rpm: 10-20
Atomisation air pressure: 2.0-5.0 kg/cm$^2$ 4. The coated core of step 3 above was dried at 35-40° C. for 15 minutes to obtain the enteric coated benzimidazole core.

D. Lubrication

1. The enteric coated benzimidazole core was fluidized with talc in a Wurster coater for 5 minutes.

2. The core of step 1 above was dried in a vacuum tray drier at 40° C. till the loss on drying is less than 1.5% w/w.

The XRD data indicated that the conversion to crystalline omeprazole/esomeprazole magnesium in 1A, 1B and 1C is less than 5% by weight.

EXAMPLE 2

| S. No | Ingredients | Quantity (mg/capsule) | |
|---|---|---|---|
| | | 2A | 2B (Reference example) |
| A) | Benzimidazole core | | |
| 1 | Non-pareil seeds (20-25) | 100.0 | 100.0 |
| 2 | Amorphous esomeprazole magnesium | 44.5 | 44.5 |
| 3 | Hydroxypropyl cellulose (HPC-L) | 20.0 | 20.0 |
| 4 | Crospovidone (Kollidon CLM) | 30.0 | 30.0 |
| 5 | Purified water | qs | qs |
| B) | Separating layer | | |
| 1 | Hydroxypropyl methylcellulose (HPMC) 5 cps | 14.98 | 14.98 |
| 2 | Polyethylene glycol 400 | 1.49 | 1.49 |
| 3 | Talc | 2.98 | 2.98 |
| 4 | Purified water | qs | qs |
| C) | Enteric coat | | |
| 1 | Methacrylic acid copolymer Type C | 39.76 | 39.76 |
| 2 | Polyethylene glycol 400 | 3.98 | 3.98 |
| 3 | Talc | 15.11 | 15.11 |
| 4 | Titanium dioxide | 4.7 | 4.7 |
| 5 | Purified water | qs | qs |
| D) | Lubrication | | |
| 1 | Talc | 0.50 | 0.50 |
| | Total | 278.0 | 278.0 |

Process

A. Preparation of Benzimidazole Core

A procedure similar to Example 1 above was followed except for the following process parameters:

EXAMPLE 2a

Inlet air temperature: 50-70° C.
Bed temperature: 40-50° C.
Pump rpm: 15-25
Atomisation air pressure: 2.0-5.0 kg/cm$^2$ Reference Example 2B Inlet air temperature: 70-80° C.
Bed temperature: 51-60° C.
Pump rpm: 15-25
Atomisation air pressure: 2.0-5.0 kg/cm$^2$ B. Separating Layer A procedure similar to Example 1 above was followed.

C. Enteric Coating

A procedure similar to Example 1 above was followed.

D. Lubrication

A procedure similar to Example 1 above was followed.

The XRD data indicated that the conversion to crystalline esomeprazole magnesium is 15-30% by weight for Example 2A and 65-100% by weight for Example 2B.

Reference Example 3

The composition was the same as Example 1A and was prepared by using a process similar to Example 1A except that the total spraying time for the preparation of the benzimidazole core was greater than 24 hrs. The XRD data indicated that the conversion to crystalline esomeprazole magnesium is 65-100% by weight.

EXAMPLE 4

|  |  | Quantity (mg/capsule) | |
|---|---|---|---|
| S. No | Ingredients | 4A | 4B (Reference example) |
| A) | Benzimidazole core | | |
| 1 | Non-pareil seeds (20-25) | 100.0 | 100.0 |
| 2 | Amorphous esomeprazole magnesium | 44.5 | 44.5 |
| 3 | Amorphous omeprazole magnesium | — | — |
| 4 | Hydroxypropyl methylcellulose | — | — |
| 5 | Hydroxypropyl cellulose (HPC-L) | 20.0 | 20.0 |
| 6 | Crospovidone (Kollidon CLM) | 30.0 | 30.0 |
| 7 | Purified water | qs | Qs |
| B) | Separating layer | | |
| 1 | Hydroxypropyl methylcellulose (HPMC) 5 cps | 14.98 | 14.98 |
| 2 | Hydroxypropyl cellulose | — | — |
| 3 | Polyethylene glycol 400 | 1.49 | 1.49 |
| 4 | Talc | 2.98 | 2.98 |
| 5 | Purified water | qs | Qs |
| C) | Enteric coat | | |
| 1 | Methacrylic Acid Copolymer Type C | 39.76 | 39.76 |
| 2 | Polyethylene glycol 400 | 3.98 | 3.98 |
| 3 | Triethyl citrate | — | — |
| 4 | Talc | 15.11 | 15.11 |
| 5 | Titanium dioxide | 4.7 | 4.7 |
| 6 | Purified water | qs | Qs |
| D) | Lubrication | | |
| 1 | Talc | 0.50 | 0.50 |
|  | Total | 278.0 | 278.0 |

Process

A process similar to Example 1A was followed except that during the preparation of the benzimidazole core the dispersion was prepared in 2 lots (4A) and 1 lot (Reference Example 4B) and the total spraying time was 24-36 hrs. The XRD data indicated that the conversion to crystalline esomeprazole magnesium is 15-30% by weight for Example 4A and 65-100% by weight for Example 4B.

EXAMPLE 5

| S. No | Ingredients | Quantity (mg/capsule) |
|---|---|---|
| A) | Benzimidazole core | |
| 1 | Non-pareil seeds (20-25) | 100.0 |
| 2 | Amorphous esomeprazole magnesium | 44.5 |
| 3 | Hydroxypropyl cellulose (HPC-L) | 20.0 |
| 4 | Crospovidone (Kollidon CLM) | 30.0 |
| 5 | Purified water | qs |
| B) | Separating layer | |
| 1 | Hydroxypropyl methylcellulose (HPMC) 5 cps | 14.98 |
| 2 | Polyethylene glycol 400 | 1.49 |
| 3 | Talc | 2.98 |
| 4 | Purified water | qs |
| C) | Enteric coat | |
| 1 | Methacrylic Acid Copolymer Dispersion (Eudragit L30D 55) equivalent to dry polymer | 28.11 |
| 2 | Polyethylene glycol 400 | 2.81 |
| 3 | Talc | 10.39 |
| 4 | Titanium dioxide | 3.32 |
| 5 | Purified water | qs |
| D) | Lubrication | |
| 1 | Talc | 0.42 |
|  | Total | 259.0 |

Process

A. Preparation of Benzimidazole Core

1. Hydroxypropyl cellulose was dissolved in purified water under mechanical stirring followed by addition of crospovidone and amorphous esomeprazole magnesium to obtain a dispersion.

2. The dispersion (prepared in six lots) was sprayed on non-pareil seeds in a Wurster coater for 12-24 hours to achieve weight buildup of approximately 94.5% using the following parameters, while continuing the slow stirring of the dispersion:

Inlet air temperature: 45-60° C.
Bed temperature: 35-40° C.
Pump rpm: 15-25
Atomisation air pressure: 2.0-5.0 kg/cm$^2$ 3. The material of step 2 above was dried at 35±5° C. for 15-30 minutes to obtain the benzimidazole core.

B. Separating Layer

1. Hydroxypropyl methylcellulose was dissolved in purified water under mechanical stirring followed by addition of polyethylene glycol and talc to obtain a coating dispersion.

2. The coating dispersion was sprayed on the benzimidazole core in a Wurster coater to achieve a weight build up of approximately 10% using the following parameters, while continuing the slow stirring of the dispersion:

Inlet air temperature: 45-60° C.
Bed temperature: 35-40° C.
Pump rpm: 10-20
Atomisation air pressure: 2.0-5.0 kg/cm$^2$ 3. The coated core of step 2 above was dried at 35±5° C. for 15-30 minutes to obtain the coated benzimidazole core.

C. Enteric Coating

1. Polyethylene glycol was dissolved in purified water under mechanical stirring followed by addition of titanium dioxide and talc to obtain a dispersion.

2. Methacrylic acid copolymer dispersion was added to the dispersion of step 1 under mechanical stirring to obtain a coating dispersion.

3. The coating dispersion of step 2 was sprayed on the coated benzimidazole core in a Wurster coater to achieve a weight build up of approximately 25% using the following parameters, while continuing the slow stirring of the dispersion:

Inlet air temperature: 40-50° C.
Bed temperature: 30-35° C.
Pump rpm: 10-20
Atomisation air pressure: 2.0-5.0 kg/cm$^2$ 4. The coated core of step 3 above was dried at 30-35° C. for 15-30 minutes to obtain the enteric coated benzimidazole core.

D. Lubrication

1. The enteric coated benzimidazole core was fluidized with talc in a Wurster coater for 3-5 minutes.

2. The core of step 1 above was dried in a vacuum tray drier at 40° C. till the loss on drying is less than 1.5% w/w.

The XRD data (FIG. 1) indicated that the conversion to crystalline esomeprazole magnesium is less than 5% by weight. The XRD data of the composition after storage at 40°

C. and 75% RH for 3 months (FIG. 2) also indicated that the conversion to crystalline esomeprazole magnesium is less than 5% by weight.

EXAMPLE 6

| S. No | Ingredients | Quantity (mg/capsule) |
|---|---|---|
| A) | Benzimidazole core | |
| 1 | Amorphous esomeprazole magnesium | 44.5 |
| 2 | Lactose monohydrate | 84.30 |
| 3 | Microcrystalline cellulose | 15.0 |
| 4 | Crospovidone Part A | 10.0 |
| 5 | Hydroxypropyl methylcellulose | 8.0 |
| 6 | Sodium lauryl sulphate | 1.2 |
| 7 | Purified water | qs |
| 8 | Crospovidone Part B | 8.0 |
| 9 | Microcrystalline cellulose (Avicel PH112) | 24.0 |
| 10 | Talc | 2.0 |
| 11 | Sodium stearyl fumarate | 3.0 |
| B) | Separating layer | |
| 1 | Hydroxypropyl methylcellulose | 10.78 |
| 2 | Polyethylene glycol | 1.09 |
| 3 | Talc | 2.13 |
| 4 | Purified water | qs |
| C) | Enteric coat | |
| 1 | Eudragit L30D-55# | 301.33 |
| 2 | Triethyl citrate | 23.13 |
| 3 | Talc | 2.71 |
| 4 | Titanium dioxide | 8.74 |
| 5 | Purified water | qs |
| | Total | 255.5 |

30% w/w aqueous dispersion

Process

A. Preparation of Benzimidazole Core

1. Amorphous esomeprazole magnesium, lactose monohydrate, microcrystalline cellulose, crospovidone (part A) and hydroxypropyl methylcellulose were blended in a Rapid mixer granulator to obtain a blend.

2. Sodium lauryl sulphate was dissolved in purified water to obtain a solution.

3. The blend of step 1 was granulated using the solution of step 2 followed by drying in a fluid bed drier at 40° C. for 4 hours and sifting to obtain granules.

4. The granules of step 3 were blended with microcrystalline cellulose (Avicel PH112), crospovidone part B, talc and sodium stearyl fumarate to obtain a final blend.

5. The final blend of step 4 was compressed into mini tablets using a rotary tablet compression machine to obtain benzimidazole core.

B. Separating Layer

1. Hydroxypropyl methylcellulose was dissolved in purified water under mechanical stirring followed by addition of polyethylene glycol and talc to obtain a coating dispersion.

2. The coating dispersion was sprayed on the benzimidazole core in a perforated coating pan using the following parameters, while continuing the slow stirring of the dispersion:

Inlet air temperature: 40-45° C.
Bed temperature: 35-38° C.
Pan speed rpm: 10-24
Pump rpm: 6-8
Atomisation air pressure: 2.0-4.0 kg/cm$^2$ C. Enteric Coating 1. Triethyl citrate was dissolved in purified water under mechanical stirring followed by addition of titanium dioxide and talc to obtain a dispersion.

2. Eudragit L30D-55 was added to the dispersion of step 1 under mechanical stirring to obtain a coating dispersion.

3. The coating dispersion of step 2 was sprayed on the coated benzimidazole core in a perforated coating pan using the following parameters, while continuing the slow stirring of the dispersion:

Inlet air temperature: 35-40° C.
Bed temperature: 32-35° C.
Pan speed rpm: 10-24
Pump rpm: 6-15
Atomisation air pressure: 2.0-4.0 kg/cm$^2$ The XRD data indicated that the conversion to crystalline esomeprazole magnesium is less than 5% by weight.

The following table shows the effect of various process parameters on the conversion of amorphous benzimidazole to crystalline form.

| 1 Processing bed temperature | | | |
|---|---|---|---|
| | Example No. | | |
| | 1A-1C | 2A | 2B |
| Bed temperature | 35-40° C. | 40-50° C. | 51-60° C. |
| % crystalline | <5% | 15-30% | 65-100% |

| 2 Number of lots of dispersion | | | |
|---|---|---|---|
| | Example No. | | |
| | 1A-1C | 4A | 4B |
| No. of lots | 4 | 2 | 1 |
| % crystalline | <5% | 15-30% | 65-100% |

| 3 Total spraying time | | |
|---|---|---|
| | Example No. | |
| | 1A-1C | 3 |
| Time | 12-24 hrs | >24 hrs |
| % crystalline | <5% | 65-100% |

The composition prepared according to the advantageous process of this invention was found to contain substantially amorphous benzimidazole compound. The composition contains less than 30% crystalline compound, preferably less than 5% more preferably below the limit of detection for example less than about 3.5%.

We claim:

1. A stable oral benzimidazole composition comprising;
   a) a benzimidazole core in the form of bead, the core comprising a pharmaceutically acceptable inert carrier coated with amorphous esomeprazole magnesium and one or more pharmaceutically acceptable additives;
   b) a separating layer surrounding the core; and
   c) an enteric coating surrounding the separating layer, wherein the composition contains less than about 30% by weight of crystalline esomeprazole magnesium after storage at 40° C. and 75% relative humidity for 3 months.

2. The composition according to claim 1, wherein the pharmaceutically acceptable additive comprises one or more of binders, diluents, disintegrants, lubricants and wetting agents.

3. The composition according to claim 2, wherein the binder comprises one or more of cellulose derivatives, gums, water-soluble vinylpyrrolidone polymers, and sugars.

4. The composition according to claim 2, wherein the diluent comprises one or more of sugars, sugar alcohols, cellulose derivatives, and starches.

5. The composition according to claim 2, wherein the disintegrant comprises one or more of sodium starch glycolate, croscarmellose sodium, crospovidone, corn starch and mixtures thereof.

6. The composition according to claim 2, wherein the lubricant comprises one or more of magnesium stearate, talc, sodium stearyl fumarate, colloidal silicon dioxide and mixtures thereof.

7. The composition according to claim 2, wherein the wetting agent comprises one or more of sodium lauryl sulphate, polysorbate 80 and mixtures thereof.

8. The composition according to claim 1, wherein the separating layer comprises a substantially water-soluble material.

9. The composition according to claim 8, wherein the substantially water-soluble material comprises one or more of a substantially water-soluble polymer and a substantially water-soluble excipient.

10. The composition according to claim 9, wherein the water-soluble polymer comprises one or more of hydroxypropyl methylcellulose, hydroxypropyl cellulose, polyvinylpyrrolidone, sodium alginate, sodium carboxymethyl cellulose, copolymer of vinylpyrrolidone and vinyl acetate.

11. The composition according to claim 9, wherein the water-soluble excipient comprises one or more of lactose, mannitol, sorbitol, sucrose and glucose.

12. A stable oral benzimidazole composition prepared according to a process, which process comprises the steps of
  a) preparing a benzimidazole core formed by dispersing amorphous esomeprazole magnesium and one or more pharmaceutically acceptable additives in an aqueous or hydroalcoholic medium to obtain a dispersion;
  b) spraying the dispersion on to a pharmaceutically acceptable inert carrier;
  c) coating the core with a separating layer; and
  d) coating the product of step (b) with an enteric coating, wherein the composition contains less than about 30% by weight of crystalline esomeprazole magnesium after storage at 40° C. and 75% relative humidity for 3 months.

13. A stable oral benzimidazole composition prepared according to a process, which process comprises the steps of
  a) preparing a benzimidazole core formed by dispersing amorphous esomeprazole magnesium and one or more pharmaceutically acceptable additives in an aqueous or hydroalcoholic medium to obtain a dispersion;
  b) spraying the dispersion on to a pharmaceutically acceptable inert carrier:
  c) coating the core with a separating layer; and
  d) coating the product of step (b) with an enteric coating, wherein said composition contains less than about 5% by weight of crystalline esomeprazole magnesium after storage at 40° C. and 75% relative humidity for 3 months.

14. The composition according to claim 1, wherein said composition contains less than about 5% by weight of crystalline esomeprazole magnesium after storage at 40° C. and 75% relative humidity for 3 months.

15. The composition according to claim 1, wherein the amount of crystallinity of the esomeprazole magnesium in the core is controlled during preparation of the composition by spraying a dispersion of the amorphous esomeprazole magnesium and one or more pharmaceutically acceptable additives in an aqueous or hydroalcoholic medium onto the pharmaceutically acceptable inert carrier at a bed temperature of less than about 50° C. for a total spraying time of less than about 24 hours to reduce conversion of the amorphous esomeprazole magnesium to crystalline esomeprazole magnesium.

16. A stable oral benzimidazole composition comprising;
  a) a benzimidazole core in the form of bead, the core comprising a pharmaceutically acceptable inert carrier coated with one or more amorphous benzimidazole compounds and one or more pharmaceutically acceptable additives, wherein during coating of the core a dispersion of the one or more amorphous benzimidazole compounds and the one or more pharmaceutically acceptable additives in an aqueous or hydroalcoholic medium was applied onto the pharmaceutically acceptable inert carrier at a bed temperature of less than about 50° C. for a total spraying time of less than about 24 hours;
  b) a separating layer surrounding the core; and
  c) an enteric coating surrounding the separating layer, wherein the composition contains less than about 30% by weight of crystalline benzimidazole, after storage at 40° C. and 75% relative humidity for 3 months.

* * * * *